United States Patent [19]
Hagmann et al.

[11] Patent Number: 4,652,637
[45] Date of Patent: Mar. 24, 1987

[54] STEROIDAL GLYCOLIPIDS

[75] Inventors: William K. Hagmann, Westfield; Mitree M. Ponpipom, Branchburg, both of N.J.

[73] Assignee: Merck & Co., Inc., Rahway, N.J.

[21] Appl. No.: 801,905

[22] Filed: Nov. 25, 1985

[51] Int. Cl.$^4$ ................................................ C07J 9/00
[52] U.S. Cl. .......................................... 536/5; 536/6.2
[58] Field of Search ............................................... 536/5

[56] References Cited
U.S. PATENT DOCUMENTS

| | | | |
|---|---|---|---|
| 4,189,471 | 2/1980 | Ponpipom et al. | 536/5 |
| 4,228,274 | 10/1980 | Ponpipom et al. | 536/4.1 |
| 4,229,441 | 10/1980 | Bugianes et al. | 536/5 |
| 4,259,324 | 3/1981 | Ponpipom et al. | 536/5 |
| 4,301,152 | 11/1981 | Ponpipom | 536/5 |

OTHER PUBLICATIONS

Chem. Abstracts, vol. 99, 1983, 122792z, Ponpipom, et al.
Chem. Abstracts, vol. 90, 1979, 23588v, Chabala, et al.
Chem. Abstracts, vol. 94, 1981, 180690x, Merck.
Carbohydrate Res., vol. 67, pp. 55–63, 1979.
J. Med. Chem., vol. 23, p. 1134 (1980).
Can. J. Chem., vol. 58, pp. 214–220 (1980).
Chem. Pharm. Bull. Jap., vol. 12, pp. 528–532 (1964).
P.N.A.S., vol. 78, pp. 7294–7298 (1981).
J. Med. Chem., vol. 15, No. 12, pp. 1284–1287 (1972).
J. Org. Chem., vol. 43, pp. 2923–2925 (1978).
Computer Literature Search Surgery, vol. 92, No 2, pp. 138–145, "Pros. for Control of Host Defenses" Infection, vol. 12, No. 3, pp. 230/182 to 234/86 (1984).

Primary Examiner—Johnnie R. Brown
Assistant Examiner—Elli Peselev
Attorney, Agent, or Firm—Robert J. North; Raymond M. Speer; Hesna J. Pfeiffer

[57] ABSTRACT

Described are derivatives of glycolipids with substituted steroids bridged via a medium length hydrocarbon chain to 1-thio-D-mannopyranoses or 1-thio-L-fucopyranoses. These compounds protect an immunocompromised human or animal host against opportunistic infection by virtue of their immunostimulant properties.

2 Claims, No Drawings

STEROIDAL GLYCOLIPIDS

BACKGROUND OF THE INVENTION

1. Field of the Invention

This invention relates to steroidal derivatives of glycolipids, in which steroids are bridged via a medium length hydrocarbon chain, to 1-thio-D-mannopyranoses or 1-thio-L-fucopyranoses as the carbohydrates, that protect an immunocompromised host against opportunistic infection.

2. Brief Description of Disclosures in the Art

The search for new immunostimulator agents for augmenting host defenses to combact infection, cancer and congenital immunodeficiency disorders is an increasingly important area of pharmaceutical endeavor. For example, see *Surgery*, Vol. 92, No. 2, pp. 138–145 (1982); *Infection*, Vol. 12 (1984) No. 117/157; and ibid., 270/82.

Glycolipids are known in the pharmaceutical arts, e.g. M. M. Ponpipom et al., in "Liposomes Technology Vol. III, Targeted Drug Delivery and Biological Interactions", ed. by G. Gregoriadis, CRC Critical Reviews, Ch. 7, pp. 95–115.

Steroidal glycosidic compounds are known in the art as being useful immunological adjuvants. For example see, U.S. Pat. No. 4,259,324; U.S. Pat. No. 4,229,441; U.S. Pat. No. 4,189,471 (all three patents being assigned to Merck & Co., Inc.); *Carbohydrate Res.* 67, pp. 55–63 (1978) by J. C. Chabala and T. Y. Shen; *J. Med. Chem.* 23, p. 1184–1188 (1980) by M. M. Ponpipom et al.; and *Can. J. Chem.* 58, pp. 214–220 (1980) by M. M. Ponpipom et al.

Glycosides are also known in the art for exhibiting pharmacological effects. For example, see U.S. Pat. No. 4,228,274; *Chem. Pharm. Bull. Jap.*, 12, 528–532 (1964); and *Proc. Nat'l Acad. Sci. USA*, Vol. 78, No. 12, pp. 7294–7298 (1981).

Another reference, *J. Med. Chem.*, 15, pp. 1284–1287 (1972), describes synthesis of epimeric 20- and 22-azacholesterols as potential therapeutic mediators for hyperfunctioning adrenal glands.

However, the above disclosures do not specifically describe glycolipids bearing steroidal substituents for use as host resistance enhancing agents, i.e., immunostimulators.

There is a continuing need and demand for safer and more effective agents in enhancing resistance to opportunistic baterial and fungal invading agents in immunocompromised hosts.

SUMMARY OF THE INVENTION

By this invention there is provided a pharmaceutical composition for enhancing host resistance in an immunocompromised individual consisting essentially of a compound of the formula:

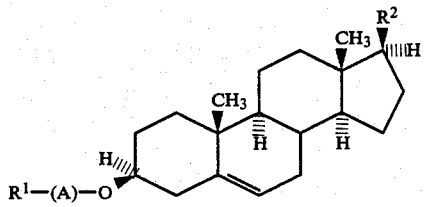

where:

$R^1$ is
  $\alpha$ or $\beta$-D-1-thiomannopyranoise,
  $\alpha$ or $\beta$-L-1-thiofucopyranose;
A is $(CH_2)_n$ where n is 5–7, or $(CH_2)_kX(CH_2)_m$ where X is O, S, NH and k, m are independently 2–4 and k+m is 4–6;
$R^2$ is
  $C_1$–$C_8$ alkyl or $C_2$–$C_{10}$ alkene;

where B is $C_1$–$C_8$ alkyl, $C_1$–$C_8$ alkoxy, $NR^3R^4$ where $R^3$ and $R^4$ are independently H, $C_1$–$C_4$ alkyl; $CH(CH_3)D$ where D is OH, $NH_2$, $NHR^5$ where $R^5$ is $C_1$–$C_{10}$ alkyl;

and pharmaceutically acceptable salts thereof, said composition also containing a pharmaceutically acceptable carrier therefor.

Also provided is a method for stimulating resistance in an immunocomprised animal or human host to bacterial or fungal infection comprising administering to said host a pharmaceutical composition as described above.

Further provided is a compound of the following formula:

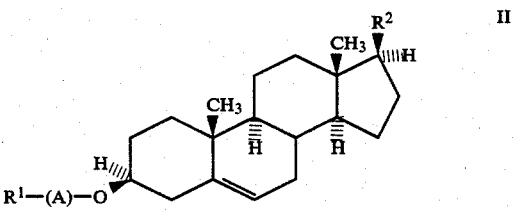

where:
$R^1$ is
  $\alpha$ or $\beta$-D-1-thiomannopyranose,
  $\alpha$ or $\beta$-L-1-thiofucopyranose;
A is $(CH_2)_n$ where n is 5–7, or $(CH_2)_kX(CH_2)_m$ where X is O or S, NH and k, m are independently 2–4 and k+m is 4–6;
$R^2$ is

where B is $C_1$–$C_8$ alkyl, $C_1$–$C_8$ alkoxy, $NR^3R^4$ where $R^3$ and $R^4$ are independently H, $C_1$–$C_4$ alkyl; $CH(CH_3)D$ where D is OH, $NH_2$, $NHR^5$ where $R^5$ is $C_1$–$C_8$ alkyl.

DETAILED DESCRIPTION OF THE INVENTION AND PREFERRED EMBODIMENTS

The glycolipid compositions described herein provide very high levels of protection against opportunistic infections in immunocompromised animals and humans.

These compositions may be used prophylactically to protect immunosuppressed animals or patients against infection by opportunistic organisms. In human medicine, the market includes surgery patients, burn victims, cancer patients receiving chemotherapy, aplastic anemics, diabetics, and military recruits. In animal health, the primary potential use markets include major segments of the worldwide economic animal populations during stressful shipping, mixing, and early life adaptation periods.

By the term "adjuvant" as used herein is meant a material which can be employed to potentiate the antibody response of specific antigenic materials. The term "antigen and antigenic material" which are also used interchangeably herein include one or more non-viable immunogenic or desensitizing (anti-allergic) agents of bacterial, viral or other origin, which when administered, produce a specific immunological response on the part of the host. The antigen component can consist of a dried powder, an aqueous solution, an aqueous suspension and the like, including mixtures of the same containing a nonviable immunogenic or desensitizing agent or agents.

By the term "immunostimulant" as used herein is meant a material which can be employed to potentiate non-specific immune response on the part of the host.

The composition of the present invention does not contain specific antigens per se. Rather, the composition contains only immunostimulants for producing a generalized and nonspecific immunological response on the part of the host, and further include acceptable salts, carriers, diluents, vehicles and the like for intravenous, subcutaneous or intraperiotoneal administration.

Referring to the above formula I the compositions of the invention include: $R^1$ is alpha- or beta-D-1-thio-mannopyranose, or alpha- or beta-L-1-thiofucopyranose. A preferred $R^1$ substituent is where the carbohydrate is $\beta$-D-mannopyranose. The hydroxyl groups on the respective glycoside can be free or can be protected by a suitable protecting group such as acetyl, benzoyl, isopropylidene, trityl, trimethylsilyl and the like. The protecting groups can easily be removed for example by mild acid or base hydrolysis, and the like, prior to administration to the host.

$R^1$ is attached via spacer arm chain A to the steroid ring at the beta 3-position. The spacer is composed of $(CH_2)_n$ where n is 5–7 carbon atoms and preferably 6. Alternately, the spacer arm can be comprised of a chain of the formula $(CH_2)_k X(CH_2)_m$ where X is oxygen, sulfur, or NH preferably oxygen; k and m are independently 2–4 carbon atoms, preferably 2; and the sum of k and m is 4–6, preferably being 4. Representative examples of A include n-pentyl, n-hexyl, n-heptyl, $CH_2CH_2$—O—$CH_2CH_2$, $CH_2CH_2$—S—$CH_2CH_2$, $CH_2CH_2CH_2$—O—$CH_2CH_2$, $CH_2CH_2$—O—$CH_2CH_2CH_2$, $CH_2CH_2$—S—$CH_2CH$, $CH_2CH_2CH_2$—S—$CH_2CH_2CH_2$ and the like. A preferred A substituent is n-hexyl.

$R^2$ is the steroidal 17-substituent preferably being in the 17-beta position of the steroid ring. $R^2$ can be $C_1$–$C_8$ alkyl including linear and branched alkyl and can be methyl, ethyl, propyl, isopropyl, isobutyl, isopentyl, and the like. Preferred is where the alkyl chain is 2,6-dimethylhexyl, being the well-known 17-beta cholesterol side chain. $R^2$ further can be $C_2$–$C_{10}$ alkene, including linear or branched alkenes including, vinyl, propenyl, isopropenyl, n-butenyl, isobutenyl, isopentenyl, allyl and the like. Preferred is the alkene: 2,6-dimethyl-3-ethyl-hex-4-enyl, being the 17-stigmasterol side chain.

$R^2$ can further be

where B is:

(a) $C_1$–$C_8$ alkyl, e.g. methyl, ethyl, propyl, isopropyl, butyl, tert-butyl, pentyl, hexyl, heptyl, octyl, isooctyl, and the like. Preferred $C_1$–$C_8$ alkyl is methyl.

(b) $C_1$–$C_8$ alkoxy for example methoxy, ethoxy, propoxy, isopropoxy, butoxy, t-butoxy, pentyloxy, hexyloxy, and the like. Preferred is methoxy.

(c) $NR^3R^4$, where $R^3$ and $R^4$ are independently selected from hydrogen, $C_1$–$C_4$ alkyl, including $NH_2$, $NHCH_3$, $NHCH_2CH_3$, $NMe_2$, $NEt_2$ and the like. Preferred is where $NR^3R^4$ group is unsubstituted amino.

(d) $CHCH_3(D)$, where D is OH, $NH_2$, $NHR^5$ where $R^5$ is $C_1$–$C_8$ alkyl, including methyl, ethyl, propyl, isopropyl and the like. Preferred is where D is OH or $NH_2$.

Representative examples include:
6-(5-Cholesten-3$\beta$-yloxy)hexyl-1-thio-$\alpha$-D-mannopyranoside;
6-(5-Cholesten-3$\beta$-yloxy)hexyl-1-thio-$\beta$-D-mannopyranoside;
6-(5-Cholesten-3$\beta$-yloxy)hexyl-1-thio-$\beta$-L-fucopyranoside;
6-(2-(5-Cholesten-3$\beta$-yloxy)ethoxy)ethyl-1-thio-$\beta$-D-mannopyranoside;
6-(Stigmasta-5,22-dien-3$\beta$-yloxy)hexyl-1-thio-$\beta$-D-mannopyranoside;
6-(Pregn-5-en-20-one-3$\beta$-yloxy)hexyl-1-thio-$\beta$-D-mannopyranoside;
6-(17$\beta$-Carbomethoxy-androst-5-en-3$\beta$-yloxy)hexyl-1-thio-$\beta$-D-mannopyranoside;
6-(17$\beta$-Carbamido-androst-5-en-3$\beta$-yloxy)-hexyl-1-thio-$\beta$-D-mannopyranoside;
6-(Pregn-5-en-20-ol-3$\beta$-yloxy)hexyl-1-thio-$\beta$-D-mannopyranoside;
6-(20S-Acetamido-pregn-5-en-3$\beta$-yloxy)-hexyl-1-thio-$\beta$-D-mannopyranoside;
6-(20R-Acetamido-pregn-5-en-3$\beta$-yloxy)-hexyl-1-thio-$\beta$-D-mannopyranoside;
6-(20S-Amino-pregn-5-en-3$\beta$-yloxy)hexyl-1-thio-$\beta$-D-mannopyranoside; or
6-(20R-Amino-pregn-5-en-3$\beta$-yloxy)hexyl-1-thio-$\beta$-D-mannopyranoside.

Referred is the compound 6-(5-cholesten-3$\beta$-yloxy)-hexyl-1-thio-$\beta$-D-mannopyranoside.

The compounds of the present invention can be prepared by reacting a per-O-acetyl-1-thio-glycopyranose, wherein the glycopyranose is L-fucose or D-mannose with a steroidal aglycone halide such as 6-(5-cholesten-3$\beta$-yloxy)hexyl iodide. Methods for making the peroacetylated thioglycopyranose are well known in the art and in general the procedure involves the reaction of a 2-acetobromoglycose in the thiourea followed by treatment of the thiouronium salt with potassium metabisulfite which is described in the reference M. M. Ponpipom et al. Can J. Chem 58, 214 (1980) hereby incorporated by reference for this particular purpose.

Methods for producing the 6-(5-cholesten-3$\beta$-yloxy)-hexyl iodide are also well known in the art and generally involve the reaction sequence of steroidal tosylate with an alcohol which is adequately described in the reference J. C. Chabala and T. Y. Shen, *Carbo Res.*, 67, 55 (1978), which is hereby incorporated by reference for this particular purpose. The corresponding steroids where stigmasterol, pregnenol, or androstanol are involved are formed by analogous procedures. Generally equimolar emounts of the per-O-acetylated thioglycopyranose and the steroidal hexyl iodide may be condensed in an inert, nonpolar solvent such as a halogenated solvent, e.g. dichloromethane or chloroform in the presence of a base such as e.g. triethylamine, 1,5-diazabicyclo[5.4.0]undec-5-ene or 1,5-diazabicyclo[4.3.0]non-5-ene. The reaction may be carried out from about 10° to about 30° C. under an inert atmosphere. Depending upon the base employed the reaction may take from about 0.5 hour to about a few days. Thus, when employing the above diazabicyclo compounds, the reaction is usually completed in from about 0.5 to about 3 hours, while when employing triethylamine the reaction is usually completed in about 1-3 days. Following the reaction the solution is washed with water and dried if the solvent was a halogenated solvent or if the solvent was tetrahydrofuran, the solution is evaporated to dryness and the residue is partitioned between dichloromethane and water. The dried solution is concentrated to a syrup which is put on a silica gel column and eluted with chloroform followed by 1-2% ethanol in chloroform. The desired fractions are pooled and evaporated to give the blocked product 6-(5-cholesten-3$\beta$-yloxy)hexyl per-O-acetyl-1-thio-glycopyranoside which is deblocked by basic ion exchange treatment or sodium methoxide in methanol to give the desired final product.

In general the steroid used has, as the A portion, the terminally halogenated alkoxy group for example 6-iodohexyloxy. Further, "A" can also consist of a terminally halogenated alkoxy-alkoxy group e.g. iodoethoxyethoxy in the 3-position of the steroidal ring.

The compounds can also alternatively be synthesized by first forming the steroidal aglycone glucopyranoside structure, in which the 17-substituent on the steroid ring is chemically blocked or is a precursor to a final product. After the condensation to form the aglycone steroidal glucopyranoside, subsequent chemistry can be carried out on the 17-group by, for example, deblocking, to form the hydroxy, reduction to form an amine, esterification to form an ester group, or de-esterification to form a carboxylic acid which can be followed by conversion to an amide or to a substituted amide or to a number carboxyl derivatives starting out originally with the ester function.

The compositions of the present invention can be conveniently be prepared in an aqueous phase in a parenterally acceptable liquid. For example, the aqueous phase can be in the form of a vaccine in which the immunostimulant is dispersed in a balanced salt solution, physiological saline solution, phosphate buffered saline solution, tissue culture fluids or other media in which the organism may have been grown. The aqueous phase may also contain preservatives and or substances conventionally incorporated in vaccine preparations.

The compounds in the subject composition of the invention are used in an amount which is deemed to be immunostimulatory to the host in inducing a generalized immune host response. In general, this amount of material would be anywhere from 2 to 120 mg/kg of host body weight and preferably 10 to 60 mg/kg of host body weight. Preferred is where the dosage is in the range of 20 to 40 mg of described compound herein to host weight.

A further characteristic of the composition is in that the compounds which are present for their immunostimulatory response preferably are in their noncrystalline form. For reasons which are not yet known or clear, when the materials are present in the crystal form they appear to be relatively inactive in producing an immunological response generalized to the same degree as the materials would have produced in the amorphous form. The crystallinity of the sample can easily be determined by X-ray diffraction analysis which should indicate the absence of a peak height pattern but simply background noise indicating an amorphous material.

Also a subject of the invention is a method for administering to an immunocompromised host a composition as described herein, containing a compound of the formula, as described, contained in a suitable carrier which may or may not have additional material such as diluents and other materials which may be deemed necessary under the circumstances. However, it is understood that the immunostimulatory preparation does not in fact include a specific antigen as a composition component. The new compounds disclosed and claimed in the present invention include those of the following formula:

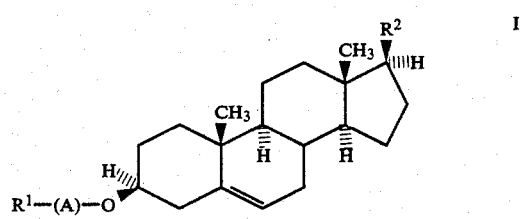

where:

$R^1$ is

α or β-D-1-thiomannopyranoside,

α or β-L-1-thiofucopyranoside;

A is $(CH_2)_n$ where n is 5-7, or $(CH_2)_k X(CH_2)_m$ where X is O or S or NH and k, m are independently 2-4 and k+m is 4-6;

$R^2$ is

where B is $C_1$-$C_8$ alkyl, $C_1$-$C_8$ alkoxy, $NR^3R^4$ where $R^3$ and $R^4$ are independently H, $C_1$-$C_4$ alkyl; $CH(CH_3)D$ where D is OH, $NH_2$, $NHR^5$ where $R^5$ is $C_1$-$C_8$ alkyl.

The descriptions and discussion of the symbols as given above or indicated are exactly the same as those described for the compounds.

Representative examples include:

6-(Pregn-5-en-20-one-3$\beta$-yloxy)hexyl-1-thio-$\beta$-D-mannopyranoside;

6-(17$\beta$-Carbomethoxy-androst-5-en-3$\beta$-yloxy)hexyl-1-thio-$\beta$-D-mannopyranoside;

6-(17$\beta$-Carbamido-androst-5-en-3$\beta$-yloxy)-hexyl-1-thio-$\beta$-D-mannopyranoside;

6-(Pregn-5-en-20-ol-3$\beta$-yloxy)hexyl-1-thio-$\beta$-D-mannopyranoside;

6-(20S-Acetamido-pregn-5-en-3$\beta$-yloxy)-hexyl-1-thio-$\beta$-D-mannopyranoside;

6-(20R-Acetamido-pregn-5-en-3$\beta$-yloxy)-hexyl-1-thio-$\beta$-D-mannopyranoside;

6-(20S-Amino-pregn-5-en-3$\beta$-yloxy)hexyl-1-thio-$\beta$-D-mannopyranoside; or 6-(20R-Amino-pregn-5-en-3$\beta$-yloxy)hexyl-1-thio-$\beta$-D-mannopyranoside.

A preferred compound is 6-(pregn-5-en-20-one-3$\beta$-yloxy)hexyl-1-thio-$\beta$-D-mannopyranoside.

EXAMPLE 1

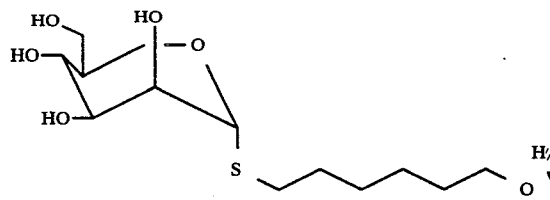 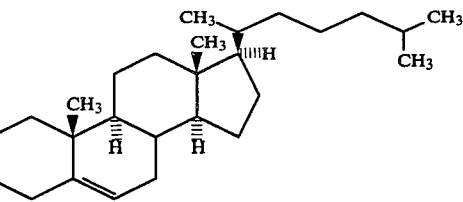

6-(5-Cholesten-3β-yloxy)hexyl 1-thio-α-D-mannopyranoside

Prepared from 2,3,4,6-tetra-O-acetyl-1-thio-α-D-mannopyranoside and cholest-5-en-3β-yl 6-iodohexyl ether as described in the literature [Chabala, J. C. and Shen, T. Y., *Carbohydr. Res.*, 67 (1978) 55–63].

Step A: Cholest-5-en-3β-yl 6-hydroxyhexyl ether

By use of the procedure described in the literature [Kosower, E. M. and Weinstein, S., *J. Am. Chem. Soc.*, 78 (1956) 4347–4354; and Davis, M., *J. Chem. Soc.*, (1962) 178–181] cholesteryl p-toluenesulfonate and 1,6-hexanediol were condensed in boiling dioxane to give cholest-5-en-3β-yl 6-hydroxyhexyl ether in 52% yield as colorless plates (from hexane), m.p. 75.9°–81° C.

Step B: Cholest-5-en-3β-yl 6-(p-toluenesulfonyloxy)hexyl ether

A solution of cholest-5-en-3β-yl 6-hydroxyhexyl ether (32 g, 66 mmol) in dry benzene (1.3 L) was treated with p-toluenesulfonic anhydride (24 g, 72.6 mmol) and 2,4,6-trimethylpyridine (11.6 ml, 8.8 g, 72 mmol), and stirred at room temperature under a dry nitrogen atmosphere for 1 hour. The mixture was filtered through a pad of Florisil and concentrated to a waxy solid (33 g, 77%).

Step C: Cholest-5-en-3β-yl 6-iodohexyl ether

A solution of cholest-5-en-3β-yl 6-(p-toluenesulfonyloxy)hexyl ether (33 g, 51 mmol) and sodium iodide (16 g, 0.106 mol) in acetone (250 ml) was refluxed for 4 hours. The solvent was removed under reduced pressure, filtered, and the collected salts washed well with ether. The filtrate was evaporated and residual yellow oil boiled in hexanes (400 ml). The solution was decanted, concentrated to 200 ml, and stored in the refrigerator for two days. The product was filtered and the mother liquors concentrated to give a total yield of 30 g (97%), m.p. 103.5°–104.5° C.

Step D: 6-(5-Cholesten-3β-yloxy)hexyl 1-thio-α-D-mannopyranoside

To a solution of 2,3,4,6-tetra-O-acetyl-1-thio-α-D-mannopyranoside (287 mg, 0.79 mmol) in dichloromethane (6 ml) was added cholest-5-en-3β-yl 6-iodohexyl ether (470 mg, 0.79 mmol) and triethylamine (0.11 ml, 0.79 mmol). After stirring under dry nitrogen atmosphere overnight at room temperature, the solvent was removed at reduced pressure and the residue chromatographed on silica gel eluted with 5–25% ethyl acetate in hexanes to give 6-(cholest-5-en-3β-yloxy)-hexyl 2,3,4,6-tetra-O-acetyl-1-thio-α-D-mannopyranoside (0.36 g, 55% yield), m.p. 103°–103.5° C. This product was dissolved in 1:1 (v/v) ethanol-tetrahydrofuran (10 ml) and was treated with a suspension of Bio-Rad AG-1-X2 OH- ion-exchange resin (2.5–3 fold excess) in ethanol (5 ml). After stirring at room temperature for 45 minutes, the resin was filtered and washed with warm tetrahydrofuran (3×5 ml), and the combined filtrates concentrated to give 6-(5-cholesten-3β-yloxy)hexyl 1thio-α-D-mannopyranoside (250 mg, 91% yield) as needles from warm tetrahydrofuran, m.p. (endothermic transitions) 64—64, 81–82, and 226°–227° C.

EXAMPLE 2

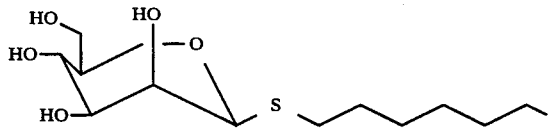 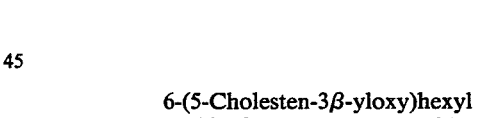

6-(5-Cholesten-3β-yloxy)hexyl 1-thio-β-D-mannopyranoside

A solution of the sodium salt of 1-thio-β-D-mannopyranoside [prepared by the procedure of Tejima, S. et al., *Chem. Pharm. Bull. Jap.*, 12 (1964) 528–532] (2.0 g, 9.1 mmol) in water (8 ml) was added to a solution of cholest-5-en-3β-yl 6-iodohexyl ether (6.0 g, 10.0 mmol) in tetrahydrofuran (40 ml) under nitrogen atmosphere. After stirring at room temperature for 24 hours, the solvent was removed by rotoevaporation and the resultant solid mass was purified by flash column chromatography [Still, W. C. et al., *J. Org. Chem.*, 43 (1978) 2923–2925] on silica gel eluted with chloroform to 5%–10% methanol/chloroform. The eluent solvent was removed by rotoevaporation to give 6-(5-cholesten-3β-yloxy)hexyl 1-thio-β-D-mannopyranoside as a white powder (6.2 g).

The reaction product was chromatographed by thin layer chromatography (TLC) on Analtech Silica Gel GHLF 250 micron plates in 10% methanol/chloroform. The resulting R$_f$ value is given below in the Table 1.

TABLE I

Thin Layer Chromatography Values for Examples

| Example No. | Rf Value | Solvent System* |
|---|---|---|
| 1 | Cited from literature. | |
| 2 | 0.54 | A |
| 3 | Not run. | |
| 4 | Cited from literature. | |
| 5A | 0.68 | B |
| 5B | 0.48 | C |
| 5C | 0.82 | C |
| 5D | Not run | — |
| 6A | 0.46 | D |
| 6B | 0.87 | D |
| 6C | 0.32 | E |
| 6D | 0.26 | A |
| 7A | 0.27 | D |
| 7B | 0.56 | D |
| 7C | 0.59 | C |
| 7D | 0.28 | A |
| 8A | 0.11 | C |
| 8B | 0.35 | C |
| 8C | 0.66 | F |
| 8D | 0.17 | A |
| 9A | 0.44 | G |
| 9B | 0.61 | G |
| 10 | 0.54 | G |
| 11A | 0.56 | C |
| 11B | 0.15(S), 0.29(R) | A |
| 11C | 0.10 | H |
| 11D | 0.12 | B |
| 11E | 0.56 | G |
| 12C | 0.20 | H |
| 12D | 0.81 | G |
| 12E | 0.60 | G |
| 13A | 0.23 | F |
| 13B | 0.69 | B |
| 13C | 0.50 | C |
| 13D | 0.20 | A |
| 13E | 0.18 | G |
| 14A–E | Not run | — |

*Solvent Systems:
A - 10% methanol/chloroform
B - 50% ethyl acetate/hexanes
C - 25% ethyl acetate/hexanes
D - 30% ethyl acetate/hexanes
E - 10% ether/hexanes
F - 10% ethyl acetate/hexanes
G - 80:22:2; chloroform:methanol:water
H - 75% ethyl acetate/hexanes

EXAMPLE 3

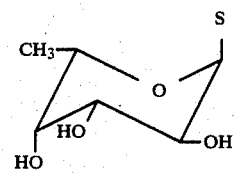
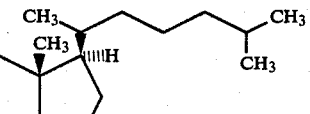

6-(5-Cholesten-3β-yloxy)hexyl
1-thio-α-L-fucopyranoside

Employing the procedure substantially as described in Example 2, but substituting for the sodium salt of 1-thio-β-D-mannopyranose, an equivalent amount of the sodium salt of 1-thio-2-L-fucopyranose, this compound is prepared.

EXAMPLE 4

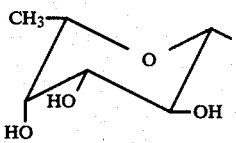
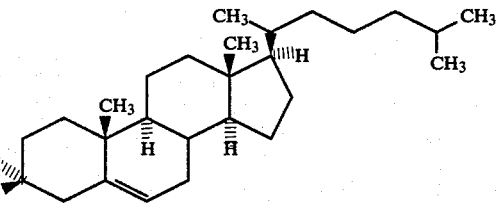

6-(5-Cholesten-3β-yloxy)hexyl
1-thio-β-L-fucopyranoside

The title compound was prepared from 2,3,4,6-O-tetra-acetyl-1-thio-β-L-fucopyranose and cholest-5-en-3β-yl 6-iodohexyl ether as described in Ponpipom, M. M. et al., Can. J. Chem., 58 (1980) 214–220.

EXAMPLE 5

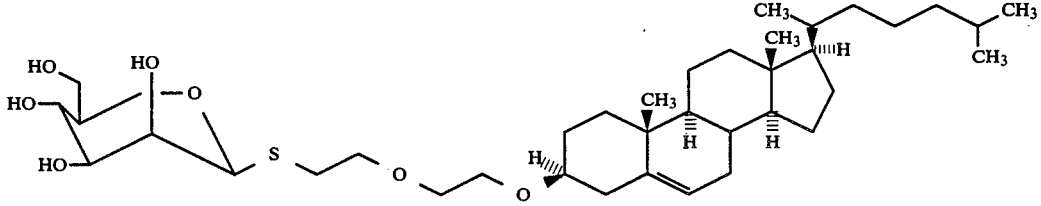

2-(2-(5-Cholesten-3β-yloxy)ethoxy)ethyl 1-thio-β-D-mannopyranoside

Employing the procedure substantially as described in Example 1, but substituting for 1,6-hexanediol, used in the preparation of cholest-5-en-3-yl 6-iodohexyl ether thereof, an equivalent amount of diethylene glycol, there was prepared in sequence:
Step A: 2-(2-(5-Cholesten-3β-yloxy)ethoxy)ethanol
Step B: 2-(5-Cholesten-3β-yloxy)ethyl 2-(p-tolyl sulfonyloxy)ethyl ether
Step C: 2-(5-Cholesten-3β-yloxy)ethyl 2-iodoethyl ether Employing the procedure substantially as described in Example 2, but substituting for cholest-5-en-3-yl 6-iodohexyl ether, an equivalent amount of 2-(5-cholesten-3-yloxy)ethyl 2-iodoethyl ether, there was produced 2-(2-(5-Cholesten-3β-yloxy)ethyl)ethyl 1-thio-β-D-mannopyranoside (Step D). TLC data and R$_f$ values are given in the above Table.

EXAMPLE 6

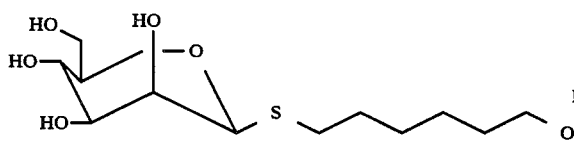

6-(Stigmasta-5,22-dien-3β-yloxy)hexyl 1-thio-β-D-mannopyranoside

Employing the procedure substantially as described in Example 1, but substituting for cholest-5-en-3β-yl, used in the preparation of cholest-5-en-3β-yl 6-iodohexyl ether, an equivalent amount of stigmasta-5,22-dien-3β-yl p-toluene-sulfonate, there was prepared in sequence:
Step A: Stigmasta-5,22-dien-3β-yl 6-hydroxyhexyl ether
Step B: Stigmasta-5,22-dien-3β-yl 6-(p-tolylsulfonyloxy)hexyl ether
Step C: Stigmasta-5,22-dien-3β-yl 6-iodohexyl ether Employing the procedure substantially as described in Example 2, but substituting for cholest-5-en-3β-yl 6-iodohexyl ether, an equivalent amount of stigmasta-5,22-dien-3β-yl 6-iodohexyl ether, there was prepared 6-(stigmasta-5,22-dien-3β-yloxy)hexyl 1-thio-β-D-mannopyranoside (Step D). TLC data and R$_f$ values are given in the above Table.

EXAMPLE 7

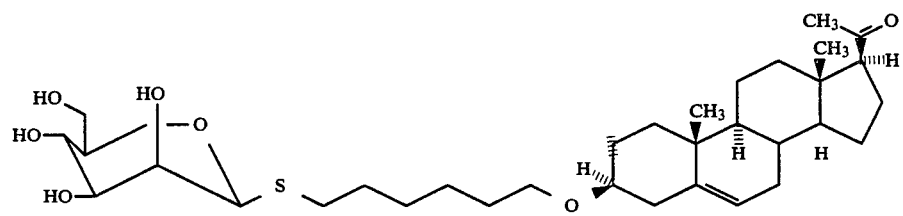

6-(Pregn-5-en-20-one-3β-yloxy)hexyl 1-thio-βD-mannopyranoside

Employing the procedure substantially as described in the literature [see Example 1], but substituting for cholesteryl p-toluenesulfonate used in the preparation of cholest-5-en-3β-yl 6-iodohexyl ether, an equivalent amount of 5-pregnen-20-one-3β-yl p-toluenesulfonate, there was prepared in sequence:
Step A: Pregn-5-en-20-one-3β-yl 6-hydroxyhexyl ether
Step B: Pregn-5-en-20-one-3β-yl 6-(p-tolylsulfonyloxy)hexyl ether
Step C: Pregn-5-3n-20-one-3β-yl 6-iodohexyl ether Employing the procedure substantially as described in Example 2, but substituting for cholest-5-en-3β-yl 6-iodohexyl ether, an equivalent amount of pregn-5-en-20-one-3β-yl 6-iodohexyl ether, there was prepared 6-(pregn-5-en-20-one-3β-yloxy)hexyl 1-thio-β-D-mannopyranoside (Step D). TLC data and R$_f$ values are given in the above Table.

EXAMPLE 8

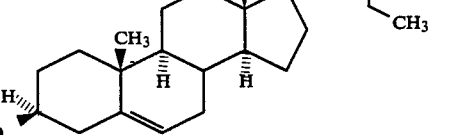

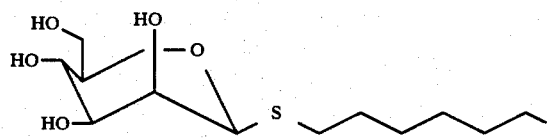
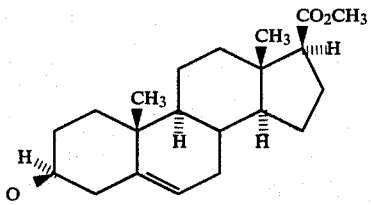

6-(17β-Carbomethoxy-androst-5-en-3β-yloxy)hexyl 1-thio-β-D-mannopyranoside

Employing the procedure substantially as described in the literature [see Example 1], but substituting for cholesteryl p-toluenesulfonate used in the preparation of cholest-5-en-3β-yl 6-iodohexyl ether, an equivalent amount of 17β-carbomethoxy-androst-5-en-3β-yl p-toluenesulfonate, there was prepared in sequence:

Step A: 17β-Carbomethoxy-androst-5-en-3β-yl 6-hydroxyhexyl ether

Step B: 17β-Carbomethoxy-androst-5-en-3β-yl 6-(p-tolylsulfonyloxy)hexyl ether

Step C: Carbomethoxy-androst-5-en-3β-yl 6-iodohexyl ether

Employing the procedure substantially as described in Example 2, but substituting for cholest-5-en-3β-yl 6-iodohexyl ether, an equivalent amount of 17β-carbomethoxy-androst-5-en-3β-yl 6-iodohexyl ether, there was prepared 6-(17β-carbomethoxy-androst-5-en-3β-yloxy)-hexyl 1-thio-β-D-mannopyranoside (Step D).

TLC data and R$_f$ values are given in the above Table.

EXAMPLE 9

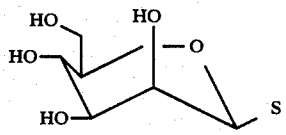
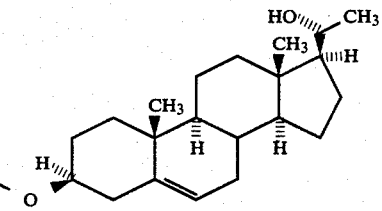

6-(17β-Carbamido-androst-5-en-3β-yloxy)hexyl 1-thio-β-D-mannopyranoside

Step A: 6-(17β-Carboxyl-androst-5-en-3β-yloxy)hexyl 1-thio-β-D-mannopyranoside

A solution of 6-(17β-carbomethoxy-androst-5-en-3β-yloxy)hexyl 1-thio-β-D-mannopyranoside (550 mg) and potassium hydroxide (85%, 110 mg) in methanol (1.4 ml) and water (0.3 ml) was refluxed for 29 hours under a nitrogen atmosphere. After cooling, 6N hydrochloric acid (3 ml) was added and the suspension filtered. The white solid was successively washed with water (5×) and dried to give the carboxylic acid (316 mg). The 200 MHz NMR spectrum in chloroform-d and the infra-red spectrum of the peracetylated derivative was in accord with the desired structure.

Step B: 6-(17β-Carbamido-androst-5-en-3β-yloxy)hexyl 1-thio-β-D-mannopyranoside

A solution of 6-(17β-carboxyl-androst-5-en-3β-yloxy)hexyl 1-thio-β-D-mannopyranoside (425 mg) in chloroform (2 ml) and toluene (2 ml) at 0° C. was treated with pyridine (0.5 ml) and oxalyl chloride (0.5 ml). After stirring at room temperature for 2 hours, the solution was added to a solution of chloroform saturated with ammonia gas. After stirring at room temperature for 2 hours, chloroform (150 ml) was added and the solution successively washed with water (3×) and dried over anhydrous sodium sulfate. The solvent was removed by rotoevaporation to give the produce as a slightly orange powder. The 200 MHz NMR spectrum in chloroform-d of the peracetylated derivative was in accord with the desired structure. TLC data and R$_f$ values given in the above Table.

EXAMPLE 10

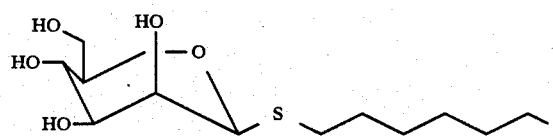

6-(Pregn-5-en-20-ol-3β-yloxy)hexyl 1-thio-β-D-mannopyranoside

Sodium borohydride (60 mg) was added to a solution of 6-(pregn-5-en-20-one-3β-yloxy)hexyl 1-thio-β-D-mannopyranoside (250 mg) in absolute ethanol (7 ml). After stirring at room temperature for 4 hours, the solution was cooled and glacial acetic acid (10 ml) was slowly added. The solution was added to chloroform (100 ml) and successively washed with water (3×), 1N sodium bicarbonate (2×), and water (1×) and dried over anhydrous sodium sulfate. The solvent was removed by rotoevaporation to give the product as a fine white solid. The 200 MHz NMR spectrum of the peracetylated derivative was in accord with the desired structure. TLC data and $R_f$ values are given in the above Table.

EXAMPLE 11

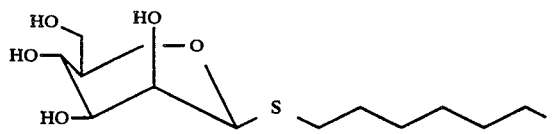 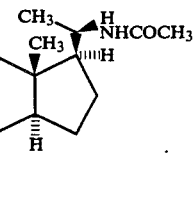

6-(20S-Acetamido-pregn-5-en-3β-yloxy)hexyl 1-thio-β-D-mannopyranoside

Step A: Pregn-5-en-20-one-3β-yl 6-(2-tetrahydropyranyloxy)hexyl ether

A solution of pregn-5-en-20-one-3β-yl 6-hydroxyhexyl ether (6.22 g ) and p-toluenesulfonic acid (20 mg) in dihydropyran (100 ml) was stirred at room temperature for 18 hours. Solid sodium bicarbonate (1 g) was added and the mixture stirred for 30 minutes. The mixture was filtered through a pad of silica gel which was subsequently washed with 50% ethyl acetate in hexanes. The solvent was removed by rotoevaporation to give the product as a clear colorless oil. TLC data and $R_f$ values for compounds A-D are given in the above Table.

Step B: 20R- and 20S-Amino-pregn-5-en-3β-yl 6-(2-tetrahydropyranyloxy)hexyl ether Employing the procedure substantially as described in the literature [Lu, M. T., et al., *J. Med. Chem.*, 15 (1972) 1284], but substituting for 3β-acetoxy-pregn-5-en-20-one in the preparation of 3β-acetoxy-20-amino-pregn-5-ene, an equivalent amount of pregn-5-en-20-one-3β-yl 6-(2-tetrahydropyranyloxy)hexyl ether, there was prepared in sequence: (1) 20-Oximo-pregn-5-en-3β-yl 6-(2-tetrahydropyranyloxy)hexyl ether and (2) 20R,S-Amino-pregn-5-en-3β-yl 6-(2-tetrahydropyranyloxy)hexyl ether. This mixture of diastereomers was separated into its respective 20R- and 20S-amino compounds by HPLC on silica gel eluted with 15% methanol in chloroform.

Step C: 20S-Acetamido-pregn-5-en-3β-yl 6-hydroxyhexyl ether

A solution of 20S-amino-pregn-5-en-3β-yl 6-(tetrahydropyranyloxy)hexyl ether (23 g) in pyridine (50 ml) and acetic anhydride (30 ml) was stirred at room temperature for 6 hours. The solvent was removed by rotoevaporation at high vacuum to give 20S-acetamido-pregn-5-en-3β-yl 6-(2-tetrahydropyranyloxy)hexyl ether which was subsequently dissolved in tetrahydrofuran (50 ml) and methanol (100 ml). Dowex 50W-8X (H+ form, 25 g) was added and the mixture stirred for 48 hours. The resin was filtered and the solvent removed by rotoevaporation to give 20S-acetamido-pregn-5-en-3β-yl 6-hydroxyhexyl ether.

Step D: 20S-Acetamido-pregn-5-en-3β-yl 6-iodohexyl ether

Employing the procedure substantially as described in the literature [see Example 1], but substituting for cholest-5-en-3β-yl 6-hydroxyhexyl ether in the preparation of cholest-5-en-3β-yl 6-iodohexyl ether, an equivalent amount of 20S-acetamido-pregn-5-en-3β-yl 6-hydroxyhexyl ether, there was prepared 20S-acetamido-pregn-5-en-3β-yl 6-(p-tolylsulfonyloxy)hexyl ether and 20S-acetamido-pregn-5-en-3β-yl 6-iodohexyl ether.

Step E: 6-(20S-Acetamido-pregn-5-en-3β-yloxy)hexyl 1-thio-β-D-mannopyranoside

Employing the procedure substantially as described in Example 2, but substituting for cholest-5-en-3β-yl 6-iodohexyl ether, an equivalent amount of 20S-acetamido-pregn-5-en-3β-yl 6-iodohexyl ether, there was prepared 6-(20S-acetamido-pregn-5-en-3β-yloxy)-hexyl 1-thio-β-D-mannopyranoside.

EXAMPLE 12

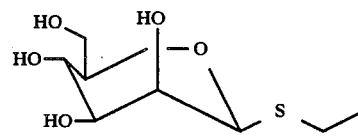 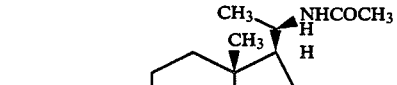

6-(20R-Acetamido-pregn-5-en-3β-yloxy)hexyl 1-thio-β-D-mannopyranoside

Employing the procedure substantially as described in Example 10, Steps C through E, but substituting for 20S-acetamido-pregn-5-en-3β-yl 6-(2-tetrahydropyranyloxy)hexyl ether, an equivalent amount of 20R-acetamido-pregn-5-en-3β-yl 6-(2-tetrahydropyranyloxy)hexyl ether, there was prepared in sequence:

Step C: 20R-Acetamido-pregn-5-en-3β-yl 6-hydroxyhexyl ether

Step D: 20R-Acetamido-pregn-5-en-3β-yl 6-iodohexyl ether

Step E: 6-(20R-Acetamido-pregn-5-en-3β-yloxy)hexyl 1-thio-β-D-mannopyranoside

TLC data and $R_f$ values for compounds C-E are given in the above Table.

EXAMPLE 13

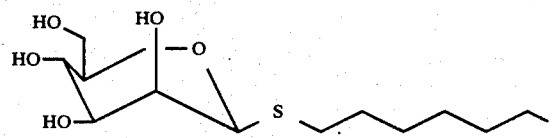
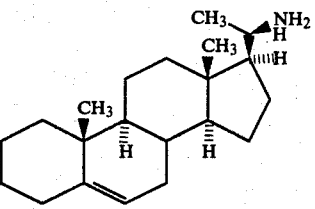

6-(20R-Amino-pregn-5-en-3β-yloxy)hexyl 1-thio-β-D-mannopyranoside

Step A: N-(2,2,2-trichloro-ethoxycarbonyl)-20R-amino-pregn-5-en-3β-yl 6-(2-tetrahydropyranyloxy)hexyl ether To a solution of 20R-amino-pregn-5-en-3β-yl 6-(2-tetrahydropyranyloxy)hexyl ether [see Example 11, Step B] (1.2 g) in pyridine (5 ml) under a dry nitrogen atmosphere was added 2,2,2-trichloro-ethoxycarbonyl chloride (1 ml). After stirring at room temperature for 6 hours, chloroform (100 ml) was added and the solution was washed successively with 1N hydrochloric acid (3×), 1N sodium bicarbonate solution (2×). The solution was dried over anhydrous sodium sulfate and the solvent removed by rotoevaporation to give the product. TLC data and $R_f$ values for compounds A–E are given in the above Table.

Step B: N-(2,2,2-trichloro-ethoxycarbonyl)-20R-amino-pregn-5-en-3β-yl 6-hydroxyhexyl ether A solution of N-(2,2,2-trichloro-ethoxycarbonyl)-20R-amino-pregn-5-en-3β-yl 6-(2-tetrahydropyranyloxy)hexyl ether (1.6 g) in methanol (10 ml) containing Dowex 50W-8X (H+ form, 3 g) was stirred at room temperature for 34 hours. Ethyl acetate (100 ml) was added, the mixture filtered, and the solution washed successively with 1N sodium bicarbonate solution (3×) and water (2×). After drying over anhydrous sodium sulfate, the solvent was removed by rotoevaporation to give the product.

Step C: N-(2,2,2-Trichloro-ethoxycarbonyl)-20R-amino-pregn-5-en-3β-yl 6-iodohexyl ether Employing the procedure substantially as described in the literature [see Example 1], but substituting for cholest-5-en-3β-yl 6-hydroxyhexyl ether in the preparation of cholest-5-en-3β-yl 6-iodohexyl ether, an equivalent amount of N-(2,2,2-trichloro-ethoxycarbonyl)-20R-amino-pregn-5-en-3β-yl 6-hydroxyhexyl ether, there was prepared this compound.

Step D: 6-(N-(2,2,2-Trichloro-ethoxycarbonyl)-20R-amino-pregn-5-en-3β-yloxy)hexyl 1-thio-β-D-mannopyranoside Employing the procedure substantially as described in Example 2, but substituting for cholest-5-en-3β-yl 6-iodohexyl ether, an equivalent amount of N-(2,2,2-trichloro-ethoxycarbonyl)-20R-amino-pregn-5-en-3β-yl 6-iodohexyl ether, there was prepared this compound.

Step E: 6-(20R-Amino-pregn-5-en-3β-yloxy)hexyl 1-thio-β-D-mannopyranoside

To a solution of 6-(N-(2,2,2-trichloroethoxycarbonyl)-20R-amino-pregn-5-en-3β-yloxy)hexyl 1-thio-β-D-mannopyranoside (2.7 g) in glacial acetic acid (10 ml) was added in portions zinc dust (3.4 g) over a 70 hour period. Tetrahydrofuran (100 ml) and methanol (20 ml) were added and the mixture was filtered. The solvent was removed by rotoevaporation and the residue dissolved in methanol (50 ml) to which was added solid sodium bicarbonate (5 g). After stirring for 15 minutes, the mixture was filtered and the solvent removed by rotoevaporation. The residue was purified by flash column chromatography on silica gel eluted with 10%–20% methanol in chloroform to give this compound.

EXAMPLE 14

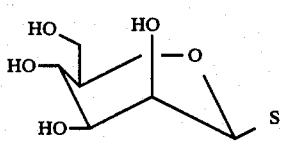

6-(20S-Amino-pregn-5-en-3β-yloxy)hexyl 1-thio-β-D-mannopyranoside

Employing the procedure substantially as described in Example 13, but substituting for 20R-amino-pregn-5-en-3β-yl 6-(2-tetrahydropyranyloxy)hexyl ether, an equivalent amount of 20S-amino-pregn-5-en-3β-yl 6-(2-tetrahydropyranyloxy)hexyl ether, there was prepared in sequence:

Step A: N-(2,2,2-trichloro-ethoxycarbonyl)-20S-amino-pregn-5-en-3β-yl 6-(2-tetrahydropyranyloxy)hexyl ether Step B: N-(2,2,2-Trichloro-ethoxycarbonyl)-20S-amino-pregn-5-en-3β-yl 6-hydroxyhexyl ether Step C: N-(2,2,2-Trichloro-ethoxycarbonyl)-20S-amino-pregn-5-en-3β-yl 6-iodohexyl ether Step D: 6-(N-(2,2,2-Trichloro-ethoxycarbonyl)-20S-amino-pregn-5-en-3β-yloxy)hexyl 1-thio-β-D-mannopyranoside Step E: 6-(20S-amino-pregn-5-en-3β-yloxy)hexyl 1-thio-β-D-mannopyranoside

EXAMPLE 15

In vivo Stimulation of Host Resistance *Pseudomonas aeruginosa* in vivo Protection Studies Groups of 15–20 CF1 female mice (Charles River Breeding, Cambridge, MA) weighing 22–28 gm were injected intraperitoneally (i.p.) with cyclophosphamide (Cytoxan; CY) at 250 mg per kg body weight. One to two hours later they were typically injected again with the test material by the route specified. Four days later, the mice were divided into groups of five, each of which were injected i.p. with a different dilution of a suspension of Pseudomonas aeruginosa (Immunotype 1). The number of survivors was determined periodically and an estimate was made of the number of CFU of Pseudomonas organisms necessary to cause 50% lethality by the cumulative method of L. J. Reed and H. Muench (*Am. J. Hygeine* 27 (1938) 493–497). A protective index (P.I.) was defined as the $LD_{50}$ for the mice receiving cyclophosphamide and the test compound divided by the $LD_{50}$ for the mice receiving cyclophosphamide alone. All control mice were injected with aqueous vehicle in the same route and schedule as the test animals.

MATERIALS

All compounds for dosing were suspended in a sterile medium referred to as "aqueous vehicle" which contains 0.9% sodium chloride, 0.5% carboxymethyl cellulose, 0.4% Tween 80, and 0.9% benzyl alcohol unless otherwise stated. Test materials were evaluated via subcutaneous (s.c.), i.p., intramuscular (i.m.), orally (p.o.), and intravenous (i.v.) routes of administration. The initial test dose was 40 mg per kg per mouse, with each active compound subsequently titrated below this level.

INFECTION OF ANIMALS

All bacteria were inoculated i.p. to induce infection in the in vivo experiments. *Candida albicans*, however, was administered i.v. Bacteria cultures were harvested in the log phase, washed with phosphate buffered saline (PBS, and resuspended in PBS containing 10% glycerol for freezing at −70° C. in 1 ml aliquots. The number of cell free units (cfu's) was determined before and after freezing. Frozen cultures were routinely thawed and diluted in sterile PBS just prior to inoculation. Viable cell counts were routinely done on thawed cultures the day of challenge to determine the number of cfu's. *Candida albicans* was stored in distilled water at room temperature. Viable cell counts were determined the day of testing.

The testing and results of 6-(5-cholesten-3β-yloxy)-hexyl-1-thio-β-D-mannopyranoside (Example 2) against various orgaisms is shown in Table 2. The results of other claimed compounds tested for protection against *Pseudomonas aeruginosa* infection are shown in Table 3.

TABLE 2

Protection from Infection by Various Organisms by 6-(5-Cholesten-3β-yloxy)hexyl-1-thio-β-D mannopyranoside.

| Treatment CY | Dose mg/kg | Organism | $LD_{50}$ Actual | P.I. (log) |
|---|---|---|---|---|
| — | — | PA | $1.89 \times 10^7$ | 5.52 |
| Control + | — | PA | $5.67 \times 10^1$ | D |
| + | 10 | PA | $3.2 \times 10^4$ | 2.75 |
| + | 20 | PA | $3.2 \times 10^5$ | 3.75 |
| + | 40 | PA | $1.22 \times 10^6$ | 4.33 |
| + | 80 | PA | $2.59 \times 10^6$ | 4.66 |
| — | — | SA | $3.38 \times 10^6$ | 1.99 |
| Control + | — | SA | $3.45 \times 10^4$ | 0 |
| + | 5 | SA | $3.38 \times 10^5$ | 0.99 |
| + | 10 | SA | $1.04 \times 10^6$ | 1.47 |
| + | 20 | SA | $2.38 \times 10^6$ | 1.83 |
| + | 40 | SA | $1.58 \times 10^7$ | 2.66 |

TABLE 2-continued

Protection from Infection by Various Organisms by 6-(5-Cholesten-3β-yloxy)hexyl-1-thio-β-D mannopyranoside.

| Treatment CY | Dose mg/kg | Organism | $LD_{50}$ Actual | P.I. (log) |
|---|---|---|---|---|
| — | — | CA | $7.88 \times 10^4$ | 1 |
| Control + | — | CA | $7.88 \times 10^3$ | 0 |
| + | 10 | CA | $3.68 \times 10^4$ | 0.67 |
| + | 20 | CA | $5.2 \times 10^4$ | 0.81 |
| + | 40 | CA | $7.88 \times 10^4$ | 1 |
| — | — | KP | $1 \times 10^8$ | 1.45 |
| Control + | — | KP | $3.53 \times 10^6$ | 0 |
| + | 40 | KP | $4.73 \times 10^7$ | 1.12 |

Key to table 2.
CY = Cytoxan
SC = Sub cutaneous administration
PA = *Pseudomonas aeruginosa* (Gram Negative bacteria)
SA = *Staphylococcus aureus* (Gram Postive bacteria)
CA = *Candida albicans* (fungus)
KP = *Klebsiella pheumoniae* (Gram Negative bacteria)
$PI = \dfrac{LD_{50} \text{ Test}}{LD_{50} \text{ CY Control}}$

TABLE 3

Stimulation of Host Resistance Against *Pseudomonas Aeruginosa*

| Compound (Same numbering as Example) | Protective Index (log) |
|---|---|
| 1. 6-(5-Cholesten-3β-yloxy)hexyl 1-thio-α-D-mannopyranoside | 1.5 |
| 2. 6-(5-Cholesten-3β-yloxy)hexyl 1-thio-β-D-mannopyranoside | 4.5 |
| 3. 6-(5-Cholesten-3β-yloxy)hexyl 1-thio-α-L-fucopyranoside | 2.8 |
| 4. 6-(5-Cholesten-3β-yloxy)hexyl 1-thio-β-L-fucopyranoside | 1.3 |
| 5. 2-(2-(5-Cholesten-3β-yloxy)ethoxy)-ethyl 1-thio-β-D-mannopyranoside | 1.7 |
| 6. 6-(Stigmasta-5,22-dien-3β-yloxy)hexyl 1-thio-β-D-mannopyranoside | 2.0 |
| 7. 6-(Pregn-5-en-20-one-3β-yloxy)hexyl 1-thio-β-D-mannopyranoside | 3.5 |
| 8. 6-(17β-Carbomethoxy-androst-5-en-3β-yloxy)hexyl 1-thio-β-D-mannopyranoside | 2.5 |
| 9. 6-(17β-Carbamido-androst-5-en-3β-yloxy)-hexyl 1-thio-β-D-mannopyranoside | 2.5 |
| 10. 6-(Pregn-5-en-20-ol-3β-yloxy)hexyl 1-thio-β-D-mannopyranoside | 1.3 |
| 11. 6-(20S—Acetamido-pregn-5-en-3β-yloxy)-hexyl 1-thio-β-D-mannopyranoside | 3.0 |
| 12. 6-(20-R—Acetamido-pregn-5-en-3β-yloxy)-hexyl 1-thio-β-D-mannopyranoside | 2.6 |
| 13. 6-(20S—Amino-pregn-5-en-3β-yloxy)hexyl 1-thio-β-D-mannopyranoside | 4.37 |
| 14. 6-(20R—Amino-pregn-5-en-3β-yloxy)hexyl 1-thio-β-D-mannopyranoside | 4.37 |

As is seen from the data, these compounds are very potent immunostimulators, protecting an immunocompromised host from death resulting from opportunistic infection.

What is claimed is:

1. A compound of the formula:

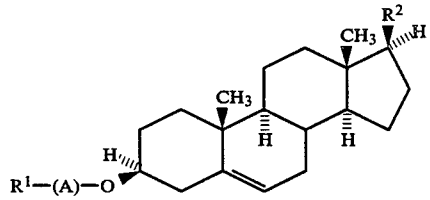

where:

R¹ is
- α or β-D-1-thiomannopyranoside,
- α or β-L-1-thiofucopyranoside;

A is $(CH_2)_n$ where n is 5–7, or $(CH_2)_k X(CH_2)_m$ where X is O, S or NH and k and m are independently 2–4 and the sum of k and m is 4–6;

R² is $$\underset{CB}{\overset{O}{\|}}$$

where B is $C_1$–$C_8$ alkyl, $C_1$–$C_8$ alkoxy, $NR^3R^4$ where $R^3$ and $R^4$ are independently H, $C_1$–$C_4$ alkyl; $CH(CH_3)D$ where D is OH, $NH_2$, $NHR^5$ where $R^5$ is $C_1$–$C_{10}$ alkyl.

2. The compound of claim 1 selected from:
- 6-(Pregn-5-en-20-one-3β-yloxy)hexyl-1-thio-β-D-mannopyranoside;
- 6-(17β-Carbomethoxy-androst-5-en-3β-yloxy)hexyl-1-thio-β-D-mannopyranoside;
- 6-(17β-Carbamido-androst-5-en-3β-yloxy)-hexyl-1-thio-β-D-mannopyranoside;
- 6-(Pregn-5-en-20-ol-3β-yloxy)hexyl-1-thio-β-D-mannopyranoside;
- 6-(20S-Acetamido-pregn-5-en-3β-yloxy)-hexyl-1-thio-β-D-mannopyranoside;
- 6-(20R-Acetamido-pregn-5-en-3β-yloxy)-hexyl-1-thio-β-D-mannopyranoside;
- 6-(20S-Amino-pregn-5-en-3β-yloxy)hexyl-1-thio-β-D-mannopyranoside; or
- 6-(20R-Amino-pregn-5-en-3β-yloxy)hexyl-1-thio-β-D-mannopyranoside.

* * * * *